US009944696B2

(12) United States Patent
DeMattos et al.

(10) Patent No.: US 9,944,696 B2

(45) Date of Patent: Apr. 17, 2018

(54) ANTI-N3PGLU AMYLOID BETA PEPTIDE ANTIBODIES AND USES THEREOF

(71) Applicant: Eli Lilly and Company, Indianapolis, IN (US)

(72) Inventors: Ronald Bradley DeMattos, Zionsville, IN (US); Jirong Lu, Indianapolis, IN (US); Ying Tang, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/402,268

(22) Filed: Jan. 10, 2017

(65) Prior Publication Data

US 2017/0204171 A1 Jul. 20, 2017

Related U.S. Application Data

(60) Provisional application No. 62/279,268, filed on Jan. 15, 2016.

(51) Int. Cl.

*C07K 16/18* (2006.01)
*A61K 39/395* (2006.01)
*A61K 39/00* (2006.01)

(52) U.S. Cl.

CPC .......... *C07K 16/18* (2013.01); *A61K 39/3955* (2013.01); *A61K 2039/505* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/92* (2013.01); *C07K 2317/94* (2013.01)

(58) Field of Classification Search

CPC ................ C07K 16/18; C07K 2317/56; C07K 2317/565; C07K 2317/51; C07K 2317/515; C07K 2317/76; C07K 2317/24; C07K 2317/92; C07K 2317/94; A61K 2039/505; A61K 39/3955; G01N 2800/2821

See application file for complete search history.

(56) References Cited

U.S. PATENT DOCUMENTS

| | | | |
|---|---|---|---|
| 7,122,374 | B1 | 10/2006 | Saido |
| 8,679,498 | B2 | 3/2014 | Lu |
| 2007/0031416 | A1 | 2/2007 | Asami |
| 2008/0299111 | A1 | 12/2008 | Sergeant |
| 2010/0021478 | A1 | 1/2010 | Demuth |

FOREIGN PATENT DOCUMENTS

| | | |
|---|---|---|
| WO | 2004013172 | 2/2004 |
| WO | 2006036291 A2 | 4/2006 |
| WO | 2008011348 | 1/2008 |
| WO | 2009149487 | 12/2009 |
| WO | 2010004434 | 1/2010 |
| WO | 2010009987 | 1/2010 |
| WO | 2011151076 | 12/2011 |

OTHER PUBLICATIONS

Oliver Wirths, et al., "Pyroglutamate Abeta pathology in APP/PS1K1 mice, sporadic and familial Alzheimer's disease cases", Journal of Neural Transmission, (2009), vol. 117(1), pp. 85-96.

Donna Wilcock, et al., Passive immunotherapy against Abeta in aged APP-transgenic mice reverses cognitive deficits and depletes parenchymal amyloid deposits in spite of increased vascular amyloid and microhemorrhage:, Journal of Neuroinflammation, (2004), vol. 1(1), p. 24.

Oliver Wirths, et al., "Identification of low molecular weight pyroglutamate Abeta oligomers in Alzheimer disease: a novel tool for therapy and diagnosis", Journal of Biological Chemistry, (2010), vol. 285(53), pp. 41517-41524.

David Brody, et al., "Active and passive immunotherapy for neurodegenerative disorders", Annual Review of Neuroscience, (2008), vol. 31, pp. 175-193.

Frederique Bard, et al., "Epitope and isotype specificities of antibodies to [beta]-amyloid peptide for protection against Alzheimer's disease-like neuropathy", Proc Natl Acad Science, (2003), vol. 100(4), pp. 2023-2028.

F. Luo, et al., "P2-304: MRI detection and time course of cerebral microhemorrhages during Abeta antibody treatment in living APP transgenic mice", Alzheimer's & Dementia: The Journal of the Alzheimer's Association, (2008), vol. 4(4), p. T461.

Margaret M. Racke, et al., "Exacerbation of cerebral amyloid angiopathy-associated microhemorrhage in amyloid precursor protein transgenic mice by immunotherapy is dependent on antibody recognition of deposited forms of amyloid beta", The Journal of Neuroscience: The Official Journal of the Socitey for Neuroscience, (2005), vol. 25(3), pp. 629-636.

T. A. Bayer, et al., "Intraneuronal Abeta as a trigger for neuron loss: Can this be translated into human pathology?", Biochemical Society Transactions, (2011), vol. 39(4), pp. 857-861.

Desikan et al., MRI measures of temporoparietal regions show differential rates of atrophy during prodromal AD. Neurology, 2008;71:819-825.

Fennema-Notestine et al., Structural MRI BIomarkers for Preclinical and Mild Alzheimer's Disease, Human Brain Mapp. Oct. 2009; 30(10): 3238-3253.

Schroeter et al., Immunotiierapy Reduces Vascular Amylold-beta in PDAPP Mice. The Journal of Neuroscience, Jul. 2, 2008 0 28(27):6787-6793.

DeMattos et al., A Plaque-Specific Antibody Clears Existing beta-amyloid Plaques in Alzheimer's Disease Mice. Neuron 76, 908-920, Dec. 6, 2012, 908-920.

*Primary Examiner* — Kimberly Ballard

(74) *Attorney, Agent, or Firm* — Megan N. Thobe; Sanjay Jivraj

(57) ABSTRACT

Antibodies to human N3pGlu Aβ, compositions comprising such N3pGlu Aβ antibodies, and methods of using such N3pGlu Aβ antibodies for the treatment of a disease characterized by deposition of Aβ including clinical or pre-clinical Alzheimer's disease, Down's syndrome, and clinical or pre-clinical cerebral amyloid angiopathy.

19 Claims, No Drawings

ANTI-N3PGLU AMYLOID BETA PEPTIDE ANTIBODIES AND USES THEREOF

The present invention relates to antibodies that bind N3pGlu Amyloid Beta peptide and their use in treating diseases related to Amyloid Beta (herein referred to as Aβ or Abeta) peptide.

The cleavage of the amyloid precursor protein results in Aβ peptides ranging in size from 38 and 43 amino acids. Conversion of Aβ from soluble to insoluble forms having high β-sheet content and the deposition of these insoluble forms as neuritic and cerebrovascular plaques in the brain has been associated with a number of conditions and diseases, including Alzheimer's disease (AD), Down's syndrome, and cerebral amyloid angiopathy (CAA).

The deposits found in plaques are comprised of a heterogeneous mixture of Aβ peptides. N3pGlu Aβ, also referred to as N3pE, pE3-42, or $A\beta_{p3-42}$, is a truncated form of Aβ peptide and is found only in plaques. N3pGlu Aβ lacks the first two amino acid residues at the N-terminus of human Aβ and has a pyroglutamate which was derived from the glutamic acid at the third amino acid position. Although N3pGlu Aβ peptide is a minor component of the deposited Aβ in the brain, studies have demonstrated that N3pGlu Aβ peptide has aggressive aggregation properties and accumulates early in the deposition cascade.

Antibodies to N3pGlu Aβ are known in the art. For example, U.S. Pat. No. 8,679,498 discloses human N3pGlu Aβ antibodies (e.g. B12L) and methods of treating diseases, such as Alzheimer's disease, with said antibodies. However, there still remains a need for N3pGlu Aβ antibodies with higher affinity, improved thermostability, reduced non-specific binding, and lower levels of immunogenicity. Such N3pGlu Aβ antibodies would provide an improved safety profile for a potential human therapeutic with pharmacokinetics for a better dosing schedule.

The antibodies within the scope of the present invention possess these desirable characteristics. The present invention provides an antibody that binds human N3pGlu Aβ, wherein said antibody comprises a light chain variable region (LCVR) having the amino acid sequence of SEQ ID NO: 9 or 10, and a heavy chain variable region (HCVR) having the amino acid sequence of SEQ ID NO: 8. In a particular embodiment, the present invention provides an antibody that binds human N3pGlu Aβ, wherein said antibody comprises a light chain variable region (LCVR) having the amino acid sequence of SEQ ID NO: 9, and a heavy chain variable region (HCVR) having the amino acid sequence of SEQ ID NO: 8. In another particular embodiment, the present invention provides an antibody that binds human N3pGlu Aβ, wherein said antibody comprises a light chain variable region (LCVR) having the amino acid sequence of SEQ ID NO: 10, and a heavy chain variable region (HCVR) having the amino acid sequence of SEQ ID NO: 8.

In an embodiment, the present invention provides an antibody that binds human N3pGlu Aβ, comprising a light chain (LC) and a heavy chain (HC), wherein the amino acid sequence of the LC is the amino acid sequence of SEQ ID NO:12 or 13, and the amino acid sequence of the HC is the amino acid sequence of SEQ ID NO:11. In a more particular embodiment, the present invention provides an antibody that binds human N3pGlu Aβ, comprising a light chain (LC) and a heavy chain (HC), wherein the amino acid sequence of the LC is the amino acid sequence of SEQ ID NO:12, and the amino acid sequence of the HC is the amino acid sequence of SEQ ID NO:11. In another particular embodiment, the present invention provides an antibody that binds human N3pGlu Aβ, comprising a light chain (LC) and a heavy chain (HC), wherein the amino acid sequence of the LC is the amino acid sequence of SEQ ID NO:13, and the amino acid sequence of the HC is the amino acid sequence of SEQ ID NO:11. In a further embodiment, the present invention provides an antibody comprising two LC and two HC, wherein the amino acid sequence of each LC is SEQ ID NO:12 or 13, and the amino acid sequence of each HC is SEQ ID NO:11. In a more particular embodiment, the present invention provides an antibody comprising two LC and two HC, wherein the amino acid sequence of each LC is SEQ ID NO:12, and the amino acid sequence of each HC is SEQ ID NO:11. In a more particular embodiment, the present invention provides an antibody comprising two LC and two HC, wherein the amino acid sequence of each LC is SEQ ID NO:13, and the amino acid sequence of each HC is SEQ ID NO:11.

The present invention also provides a N3pGlu Aβ antibody comprising an LCVR and an HCVR, wherein said LCVR comprises LCDR1, LCDR2, and LCDR3, and wherein said HCVR comprises HCDR1, HCDR2, and HCDR3, and wherein the amino acid sequences of said CDRs are SEQ ID NO:4 for LCDR1, SEQ ID NO:6 for LCDR2, SEQ ID NO:7 for LCDR3, SEQ ID NO:1 for HCDR1, SEQ ID NO:2 for HCDR2, and SEQ ID NO:3 for HCDR3

The present invention further provides pharmaceutical compositions comprising an antibody of the present invention and one or more pharmaceutically acceptable carriers, diluents or excipients. Further, the present invention provides a method of treating a disease characterized by deposition of Aβ, comprising administering to a patient in need thereof a pharmaceutical composition of the present invention. Particularly, the present invention provides a method of treating or preventing clinical or pre-clinical Alzheimer's disease, Down's syndrome, and clinical or pre-clinical CAA comprising administering to a patient in need thereof an effective amount of an antibody of the present invention. More particularly, the present invention provides a method of treating or preventing a condition selected from prodromal AD (sometimes also referred to as Aβ-related mild cognitive impairment, or MCI), mild AD, moderate AD and severe AD, comprising administering to a patient in need thereof a pharmaceutical composition of the present invention.

In another embodiment the present invention provides a method of slowing cognitive decline in a patient diagnosed with pre-clinical Alzheimer's disease or clinical Alzheimer's disease, comprising administering a pharmaceutical composition of the present invention. More particularly, the present invention further provides a method of slowing cognitive decline in a patient diagnosed with a condition selected from prodromal AD, mild AD, moderate AD and severe AD, comprising administering a pharmaceutical composition of the present invention.

In another embodiment the present invention provides a method of slowing functional decline in a patient diagnosed with pre-clinical Alzheimer's disease or clinical Alzheimer's disease, comprising administering a pharmaceutical composition of the present invention. More particularly, the present invention provides a method of slowing functional decline in a patient diagnosed with a condition selected from prodromal AD, mild AD, moderate AD and severe AD, comprising administering a pharmaceutical composition of the present invention.

In another embodiment the present invention provides a method of reducing brain Aβ amyloid plaque load in a patient diagnosed with pre-clinical or clinical Alzheimer's disease, comprising administering a pharmaceutical composition of the present invention. More particularly, the present invention provides a method of reducing brain Aβ amyloid plaque load in a patient diagnosed with a condition selected from prodromal AD, mild AD, moderate AD, and severe AD, comprising administering a pharmaceutical composition of the present invention.

In another embodiment the present invention provides a method of preventing memory loss or cognitive decline in asymptomatic patients with low levels of Aβ1-42 in the cerebrospinal fluid (CSF) or Aβ plaques in the brain comprising administering to the said patient a pharmaceutical composition of the present invention.

In another embodiment the present invention provides a method of treating asymptomatic patients known to have an Alzheimer's disease-causing genetic mutation, comprising administering to the said patient a pharmaceutical composition of the present invention. In a particular embodiment, the present invention provides a method of treating asymptomatic patients known to have a PSEN1 E280A Alzheimer's disease-causing genetic mutation (Paisa mutation), comprising administering to the said patient a pharmaceutical composition of the present invention. In another particular embodiment, the present invention provides a method of treating asymptomatic patients with a genetic mutation that causes autosomal-dominant Alzheimer's disease, comprising administering to the said patient a pharmaceutical composition of the present invention.

In another embodiment the present invention provides a method of preventing memory loss or cognitive decline in asymptomatic patients known to have an Alzheimer's disease-causing genetic mutation, comprising administering to the said patient a pharmaceutical composition of the present invention. In a particular embodiment, the present invention provides a method of preventing memory loss or cognitive decline in asymptomatic patients known to have a PSEN1 E280A Alzheimer's disease-causing genetic mutation (Paisa mutation), comprising administering to the said patient a pharmaceutical composition of the present invention. In another particular embodiment, the present invention provides a method of preventing memory loss or cognitive decline in asymptomatic patients with a genetic mutation that causes autosomal-dominant Alzheimer's disease, comprising administering to the said patient a pharmaceutical composition of the present invention.

In another embodiment the present invention provides a method of slowing cognitive decline in an asymptomatic patient known to have an Alzheimer's disease-causing genetic mutation, comprising administering to the said patient a pharmaceutical composition of the present invention. In a particular embodiment, the present invention provides a method of slowing cognitive decline in asymptomatic patients known to have a PSEN1 E280A Alzheimer's disease-causing genetic mutation (Paisa mutation), comprising administering to the said patient a pharmaceutical composition of the present invention. In another particular embodiment, the present invention provides a method of slowing cognitive decline in asymptomatic patients with a genetic mutation that causes autosomal-dominant Alzheimer's disease, comprising administering to the said patient a pharmaceutical composition of the present invention.

The present invention also provides an antibody of the present invention for use in therapy. In an embodiment, the present invention provides an antibody of the present invention for use in the treatment of a disease characterized by deposition of Aβ. In another embodiment, the present invention provides an antibody of the present invention for use in treatment of clinical or pre-clinical Alzheimer's disease, Down's syndrome, and clinical or pre-clinical cerebral amyloid angiopathy. In another embodiment, the present invention provides an antibody of the present invention for use in treatment of a condition selected from prodromal AD, mild AD, moderate AD and severe AD. In another embodiment, the present invention provides an antibody of the present invention for use in slowing cognitive decline in a patient diagnosed with a condition selected from clinical or pre-clinical Alzheimer's disease, Down's syndrome, and clinical or pre-clinical cerebral amyloid angiopathy. In another embodiment, the present invention provides an antibody of the present invention for use in slowing cognitive decline in a patient diagnosed with a condition selected from prodromal AD, mild AD, moderate AD and severe AD.

Further, the present invention provides a pharmaceutical composition comprising an antibody of the present invention for use in therapy. In an embodiment, the present invention provides a pharmaceutical composition comprising an antibody for use in the treatment of a disease characterized by deposition of Aβ.

The present invention also provides the use of an antibody of the present invention in the manufacture of a medicament for the treatment of a disease characterized by deposition of Aβ. In an embodiment, the present invention provides the use of an antibody of the present invention in the manufacture of a medicament for the treatment of clinical or pre-clinical Alzheimer's disease, Down's syndrome, and clinical or pre-clinical cerebral amyloid angiopathy. In an embodiment, the present invention provides the use of an antibody of the present invention in the manufacture of a medicament for the treatment of prodromal AD, mild AD, moderate AD or severe AD. In another embodiment, the present invention provides the use of an antibody of the present invention in the manufacture of a medicament for slowing cognitive decline in a patient diagnosed with a condition selected from clinical or pre-clinical Alzheimer's disease, Down's syndrome, and clinical or pre-clinical cerebral amyloid angiopathy. In another embodiment, the present invention provides the use of an antibody of the present invention in the manufacture of a medicament for slowing cognitive decline in a patient diagnosed with a condition selected from prodromal AD, mild AD, moderate AD and severe AD.

In an embodiment, the present invention provides a DNA molecule comprising a polynucleotide sequence encoding a polypeptide having the amino acid sequence of SEQ ID NO: 8. In an embodiment, the present invention provides a DNA molecule comprising a polynucleotide sequence encoding a polypeptide having the amino acid sequence of SEQ ID NO:9. In an embodiment, the present invention provides a DNA molecule comprising a polynucleotide sequence encoding a polypeptide having the amino acid sequence of SEQ ID NO:10. In a further embodiment, the present invention provides a DNA molecule comprising a polynucleotide sequence encoding a polypeptide having the amino acid sequence of SEQ ID NO:8, and comprising a polynucleotide sequence encoding a polypeptide having the amino acid sequence of SEQ ID NO:9. In another embodiment, the present invention provides a DNA molecule comprising a polynucleotide sequence encoding a polypeptide having the amino acid sequence of SEQ ID NO:8, and comprising a polynucleotide sequence encoding a polypeptide having the amino acid sequence of SEQ ID NO:10.

In an embodiment, the present invention provides a DNA molecule comprising a polynucleotide sequence encoding a polypeptide having the amino acid sequence of SEQ ID NO:11. In an embodiment, the present invention provides a DNA molecule comprising a polynucleotide sequence encoding a polypeptide having the amino acid sequence of SEQ ID NO:12. In an embodiment, the present invention provides a DNA molecule comprising a polynucleotide sequence encoding a polypeptide having the amino acid sequence of SEQ ID NO:13. In a further embodiment, the present invention provides a DNA molecule comprising a polynucleotide sequence encoding a polypeptide having the amino acid sequence of SEQ ID NO:11, and comprising a polynucleotide sequence encoding a polypeptide having the amino acid sequence of SEQ ID NO:12. In another embodiment, the present invention provides a DNA molecule comprising a polynucleotide sequence encoding a polypeptide having the amino acid sequence of SEQ ID NO:11, and comprising a polynucleotide sequence encoding a polypeptide having the amino acid sequence of SEQ ID NO:13. In another embodiment, the present invention provides a DNA molecule comprising a polynucleotide sequence encoding a polypeptide having the amino acid sequence of SEQ ID NO:11, and a DNA molecule comprising a polynucleotide sequence encoding a polypeptide having the amino acid sequence of SEQ ID NO:12. In another embodiment, the present invention provides a DNA molecule comprising a polynucleotide sequence encoding a polypeptide having the amino acid sequence of SEQ ID NO:11, and a DNA molecule comprising a polynucleotide sequence encoding a polypeptide having the amino acid sequence of SEQ ID NO:13. In a particular embodiment the polynucleotide sequence encoding a polypeptide having the amino acid sequence of SEQ ID NO:11 is SEQ ID NO:14 and the polynucleotide sequence encoding a polypeptide having the amino acid sequence of SEQ ID NO:12 is SEQ ID NO:15. In a particular embodiment the polynucleotide sequence encoding a polypeptide having the amino acid sequence of SEQ ID NO:11 is SEQ ID NO:14 and the polynucleotide sequence encoding a polypeptide having the amino acid sequence of SEQ ID NO:13 is SEQ ID NO:16.

Further, the present invention provides a mammalian cell comprising a DNA molecule comprising a polynucleotide sequence encoding a polypeptide having the amino acid sequence of SEQ ID NO:11 and a DNA molecule comprising a polynucleotide sequence encoding a polypeptide having the amino acid sequence of SEQ ID NO:12. Preferably the mammalian cell comprises a DNA molecule comprising a polynucleotide sequence encoding a polypeptide having the amino acid sequence of SEQ ID NO:11 and a polypeptide having the amino acid sequence SEQ ID NO:12. The present invention also provides a mammalian cell comprising a DNA molecule comprising a polynucleotide sequence encoding a polypeptide having the amino acid sequence of SEQ ID NO:11 and a DNA molecule comprising a polynucleotide sequence encoding a polypeptide having the amino acid sequence of SEQ ID NO:13. Preferably the mammalian cell comprises a DNA molecule comprising a polynucleotide sequence encoding a polypeptide having the amino acid sequence of SEQ ID NO:11 and a polypeptide having the amino acid sequence of SEQ ID NO:13. In an embodiment the mammalian cell line is a Chinese Hamster Ovary (CHO) or Hamster embryonic kidney (HEK) cell line.

The present invention also provides a mammalian cell comprising a DNA molecule comprising a polynucleotide sequence encoding a polypeptide having the amino acid sequence of SEQ ID NO:8 and/or a DNA molecule comprising a polynucleotide sequence encoding a polypeptide having the amino acid sequence of SEQ ID NO:9, wherein the cell is capable of expressing an antibody comprising a HCVR having the amino acid sequence of SEQ ID NO:8 and a LCVR having the amino acid sequence of SEQ ID NO:9. Preferably the mammalian cell comprises a DNA molecule comprising a polynucleotide sequence encoding a polypeptide having the amino acid sequence of SEQ ID NO:8 and a polypeptide having the amino acid sequence SEQ ID NO:9. The present invention also provides a mammalian cell comprising a DNA molecule comprising a polynucleotide sequence encoding a polypeptide having the amino acid sequence of SEQ ID NO:8 and/or a DNA molecule comprising a polynucleotide sequence encoding a polypeptide having the amino acid sequence of SEQ ID NO:10, wherein the cell is capable of expressing an antibody comprising a HCVR having the amino acid sequence of SEQ ID NO:8 and a LCVR having the amino acid sequence of SEQ ID NO:10. Preferably the mammalian cell comprises a DNA molecule comprising a polynucleotide sequence encoding a polypeptide having the amino acid sequence of SEQ ID NO:8 and a polypeptide having the amino acid sequence SEQ ID NO:10. In an embodiment the mammalian cell line is a CHO or HEK cell line.

In another embodiment, the present invention provides a process for producing an antibody comprising a LCVR having an amino acid sequence of SEQ ID NO:9 and a HCVR having an amino acid sequence of SEQ ID NO:8, wherein the process comprises cultivating a mammalian cell comprising a DNA encoding an LCVR having an amino acid sequence of SEQ ID NO:9 and/or a DNA encoding an HCVR having an amino acid sequence of SEQ ID NO:8 under conditions such that the antibody is expressed, and recovering the expressed antibody. The invention includes an antibody obtainable by the process of the invention as described immediately above. The present invention also provides a process for producing an antibody comprising a LCVR having an amino acid sequence of SEQ ID NO:10 and a HCVR having an amino acid sequence of SEQ ID NO:8, wherein the process comprises cultivating a mammalian cell comprising a DNA encoding an LCVR having an amino acid sequence of SEQ ID NO:10 and/or a HCVR having an amino acid sequence of SEQ ID NO:8 under conditions such that the antibody is expressed, and recovering the expressed antibody. The invention includes an antibody obtainable by the process of the invention as described immediately above.

In another embodiment, the present invention provides a process for producing an antibody comprising a LC having an amino acid sequence of SEQ ID NO:12 and a HC having an amino acid sequence of SEQ ID NO:11, wherein the process comprises cultivating a mammalian cell comprising a DNA encoding a LC having an amino acid sequence of SEQ ID NO:12 and/or a HC having an amino acid sequence of SEQ ID NO:11 under conditions such that the antibody is expressed, and recovering the expressed antibody. The invention includes an antibody obtainable by the process of the invention as described immediately above. The present invention also provides a process for producing an antibody comprising a LC having an amino acid sequence of SEQ ID NO:13 and a HC having an amino acid sequence of SEQ ID NO:11, wherein the process comprises cultivating a mammalian cell comprising a DNA encoding a LC having an amino acid sequence of SEQ ID NO:13 and/or a HC having an amino acid sequence of SEQ ID NO:11 under conditions such that the antibody is expressed, and recovering the expressed antibody. The invention includes an antibody obtainable by the process of the invention as described immediately above.

The present invention includes a process for producing an antibody, which antibody comprises two HC and two LC, in which the amino sequence of each of the two HC is SEQ ID NO:11, and the amino acid sequence of each of the two LC is SEQ ID NO:12, and which process comprises: a) cultivating a mammalian cell of the invention, as described above, under conditions such that the antibody is expressed, and b) recovering the expressed antibody. The invention includes an antibody obtainable by the process of the invention as described immediately above. The present invention also includes a process for producing an antibody, which antibody comprises two HC and two LC, in which the amino sequence of each of the two HC is SEQ ID NO:11 and the amino acid sequence of each of the two LC is SEQ ID NO:13, and which process comprises: a) cultivating a mammalian cell of the invention, as described above, under conditions such that the antibody is expressed, and b) recovering the expressed antibody. The invention includes an antibody obtainable by the process of the invention as described immediately above.

The antibodies of the present invention bind to N3pGlu Aβ. The sequence of N3pGlu Aβ is the amino acid sequence of SEQ ID NO:17.

As used herein, an "antibody" is an immunoglobulin molecule comprising two Heavy Chain (HC) and two Light Chain (LC) interconnected by disulfide bonds. The amino terminal portion of each LC and HC includes a variable region responsible for antigen recognition via the complementarity determining regions (CDRs) contained therein. The CDRs are interspersed with regions that are more conserved, termed framework regions. Assignment of amino acids to CDR domains within the LCVR and HCVR regions of the antibodies of the present invention is based on the well-known Kabat numbering convention (Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991)), and North numbering convention (North et al., A New Clustering of Antibody CDR Loop Conformations, Journal of Molecular Biology, 406:228-256 (2011)). Following the above method, the CDRs of the present invention were determined (Table 1).

The antibodies of the present invention include kappa LC and IgG HC. In a particular embodiment, the antibodies of the present invention are IgG1.

The antibodies of the present invention are monoclonal antibodies ("mAbs"). Monoclonal antibodies can be produced, for example, by hybridoma technologies, recombinant technologies, phage display technologies, synthetic technologies, e.g., CDR-grafting, or combinations of such or other technologies known in the art. In another embodiment of the present invention, the antibody, or the nucleic acid encoding the same, is provided in isolated form. As used herein, the term "isolated" refers to a protein, peptide or nucleic acid that is not found in nature and is free or substantially free from other macromolecular species found in a cellular environment. "Substantially free", as used herein, means the protein, peptide or nucleic acid of interest comprises more than 80% (on a molar basis) of the macromolecular species present, preferably more than 90% and more preferably more than 95%.

Following expression and secretion of the antibody, the medium is clarified to remove cells and the clarified media is purified using any of many commonly-used techniques. The purified antibody may be formulated into pharmaceutical compositions according to well-known methods for formulating proteins and antibodies for parenteral administration, particularly for subcutaneous, intrathecal, or intravenous administration. The antibody may be lyophilized, together with appropriate pharmaceutically-acceptable excipients, and then later reconstituted with a water-based diluent prior to use. Alternatively, the antibody may be formulated in an aqueous solution and stored for up to 1-3 years prior to use. In either case, the stored form and the injected form of the pharmaceutical compositions of the antibody will contain a pharmaceutically-acceptable excipient or excipients, which are ingredients other than the antibody. Whether an ingredient is pharmaceutically-acceptable depends on its effect on the safety and effectiveness or on the safety, purity, and potency of the pharmaceutical composition. If an ingredient is judged to have a sufficiently unfavorable effect on safety or effectiveness (or on safety, purity, or potency) to warrant it not being used in a composition for administration to humans, then it is not pharmaceutically-acceptable to be used in a pharmaceutical composition of the antibody.

A pharmaceutical composition comprising an antibody of the present invention can be administered to a patient at risk for, or exhibiting, diseases or disorders as described herein by parental routes (e.g., subcutaneous, intravenous, intraperitoneal, intramuscular). Subcutaneous and intravenous routes are preferred. A pharmaceutical composition of the present invention contains an "effective" amount of an antibody of the present invention. An effective amount refers to an amount necessary (at dosages and for periods of time and for the means of administration) to achieve the desired therapeutic result. An effective amount of the antibody may vary according to factors such as the disease state, age, sex, and weight of the individual, and the ability of the antibody to elicit a desired response in the individual. An effective amount can be readily determined by the attending diagnostician or health care professional, as one skilled in the art, by using known techniques and by observing results. Frequency of dosing is dependent on actual pharmacokinetics and pharmacodynamics in humans. Duration of treatment will vary depending on many factors and it will be determined by the patient's diagnostician or treating health care provider, based on experience and skill in the art. Frequency and duration of treatment may vary by indication. The terms "treatment," "treating" or "to treat" and the like include restraining, slowing or stopping the progression or severity of an existing symptom, condition, disease, or disorder in a patient. The term "patient" refers to a human.

The term "prevention" means prophylactic administration of the antibody of the present invention to an asymptomatic patient or a patient with pre-clinical Alzheimer's disease to prevent progression of the disease.

The term "disease characterized by deposition of Aβ," is a disease that is pathologically characterized by Aβ deposits in the brain or in brain vasculature. This includes diseases such as Alzheimer's disease, Down's syndrome, and cerebral amyloid angiopathy. A clinical diagnosis, staging or progression of Alzheimer's disease can be readily determined by the attending diagnostician or health care professional, as one skilled in the art, by using known techniques and by observing results. This generally includes some form of brain plaque imagining, mental or cognitive assessment (e.g. Clinical Dementia Rating-summary of boxes (CDR-SB), Mini-Mental State Exam (MMSE) or Alzheimer's Disease Assessment Scale-Cognitive (ADAS-Cog)) or functional assessment (e.g. Alzheimer's Disease Cooperative Study-Activities of Daily Living (ADCS-ADL). "Clinical Alzheimer's disease" as used herein is a diagnosed stage of Alzheimer's disease. It includes conditions diagnosed as prodromal Alzheimer's disease, mild Alzheimer's disease, moderate Alzheimer's disease and severe Alzheimer's disease. The term "pre-clinical Alzheimer's disease" is a stage that precedes clinical Alzheimer's disease, where measurable changes in biomarkers (such as CSF Aβ42 levels or deposited brain plaque by amyloid PET) indicate the earliest signs of a patient with Alzheimer's pathology, progressing to clinical Alzheimer's disease. This is usually before symptoms such as memory loss and confusion are noticeable.

The following Examples and assays demonstrate that the antibodies of the present invention are useful for treating a disease characterized by deposition of Aβ, such as of Alzheimer's disease, Down's syndrome, and CAA. It should be understood however, that the following Examples are set forth by way of illustration and not limitation, and that various modifications may be made by one of ordinary skill in the art.

EXAMPLES

Expression and Purification of Engineered N3pGlu Aβ Antibodies

N3pGlu Aβ antibodies of the present invention can be expressed and purified essentially as follows. A glutamine synthetase (GS) expression vector containing the DNA sequence encoding the LC amino acid sequence of SEQ ID NO: 12 or 13, and the DNA sequence encoding the HC amino acid sequence of SEQ ID NO:11 is used to transfect a Chinese hamster ovary cell line (CHO) by electroporation. The expression vector encodes an SV Early (Simian Virus 40E) promoter and the gene for GS. Post-transfection, cells undergo bulk selection with 0-50 μM L-methionine sulfoximine (MSX). Selected bulk cells or master wells are then scaled up in serum-free, suspension cultures to be used for production.

Clarified medium, into which the antibody has been secreted, is applied to a Protein A affinity column that has been equilibrated with a compatible buffer, such as phosphate buffered saline (pH 7.4). The column is washed with 1M NaCl to remove nonspecific binding components. The bound N3pGlu Aβ antibody is eluted, for example, with sodium citrate at pH (approx.) 3.5 and fractions are neutralized with 1M Tris buffer. N3pGlu Aβ antibody fractions are detected, such as by SDS-PAGE or analytical size-exclusion, and then are pooled. N3pGlu Aβ antibody of the present invention is concentrated in either PBS buffer at pH 7.4 or 10 mM NaCitrate buffer, 150 mM NaCl at pH around 6. The final material can be sterile filtered using common techniques. The purity of N3pGlu Aβ antibody is greater than 95%. N3pGlu Aβ antibody of the present invention may be immediately frozen at −70° C. or stored at 4° C. for several months. Amino acid SEQ ID NOs for exemplified antibodies of the present invention are shown below.

TABLE 1

Amino acid sequences of exemplified N3pGlu Aβ antibodies.

| Antibody | Antibody SEQ ID NOs | | | |
|---|---|---|---|---|
| | Light Chain | Heavy Chain | LCVR | HCVR |
| I | 12 | 11 | 9 | 8 |
| II | 13 | 11 | 10 | 8 |

TABLE 1-continued

Amino acid sequences of exemplified N3pGlu Aβ antibodies.

| Antibody | Antibody SEQ ID NOs | | |
|---|---|---|---|
| | LCDR1 | LCDR2 | LCDR3 |
| I | 4 | 6 | 7 |
| II | 4 | 5 | 7 |

| Antibody | Antibody SEQ ID NOs | | |
|---|---|---|---|
| | HCDR1 | HCDR2 | HCDR3 |
| I and II | 1 | 2 | 3 |

Binding Affinity and Kinetics

The binding affinity and kinetics of N3pGlu Aβ antibody to pE3-42 Aβ peptide or to Aβ 1-40 peptide is measured by surface plasmon resonance using Biacore® 3000 (GE Healthcare). The binding affinity is measured by capturing N3pGlu Aβ antibody via immobilized protein A on a Biacore® CM5 chip, and flowing pE3-42 Aβ peptide or Aβ 1-40 peptide, starting from 100 nM in 2-fold serial dilution down to 3.125 nM. The experiments are carried out at 25° C. in HBS-EP buffer (GE Healthcare BR100669; 10 mM HEPES, 150 mM NaCl, 3 mM EDTA, 0.05% surfactant P20, pH 7.4).

For each cycle, antibody is captured with 5 μL injection of antibody solution at a 10 μg/mL concentration with 10 μL/min. flow rate, The peptide is bound with 250 μL injection at 50 μl/min, and then dissociated for 10 minutes. The chip surface is regenerated with 5 μL injection of glycine buffer at pH 1.5 at 10 μL/mL flow rate. The data is fit to a 1:1 Langmiur binding model to derive $k_{on}$, $k_{off}$, and to calculate $K_D$. Following procedures essentially as described above, the following parameters (shown in Table 2) were observed.

TABLE 2

Binding affinity and kinetics.

| Antibody | $k_{on}$ (×10$^5$1/MS) | $k_{off}$(×10$^{-4}$1/s) | $K_D$ (nM) |
|---|---|---|---|
| I | 1.39 | 1.31 | 0.71 |
| II | 3.63 | 1.28 | 0.35 |

No appreciable binding to Aβ 1-40 was detected, indicating that Antibody I and Antibody II bound specifically to pE3-42 Aβ peptide as compared to Aβ 1-40.

Thermostability

To determine antibody stability at stressed conditions (i.e. elevated temperature and low pH), clarified media containing antibody of the present invention is adjusted to pH 7.4 or pH 5.0 with PBS or 100 mM sodium citrate, respectively. Samples are sealed and incubated at 65° C. for 60 minutes and then cooled down on ice. Protein aggregates in samples are precipitated by centrifugation, and the clear supernatants are transferred to a new plate and neutralized to pH 7.4 by a 50-fold dilution into PBS buffer. Antigen (pE3-42) binding activity is measured and calculated against an un-stressed sample to determine percentage of activity remaining.

Following procedures essentially as described above, the following data were obtained.

TABLE 3

| Percentage of antigen binding activity following stress. | | |
|---|---|---|
| Antibody | pH 7.4 (%) | pH 5.0 (%) |
| I | Not determined | 60.2 |
| II | 91.6 | 71.2 |
| B12L | 62.1 | 11.1 |

As demonstrated in Table 3, Antibody I and Antibody II have increased thermostability as compared to B12L.

Ex Vivo Target Engagement

To determine ex vivo target engagement on brain sections from a fixed PDAPP brain, immunohistochemical analysis is performed with exogenously added N3pGlu Aβ antibodies of the present invention. Cryostat serial coronal sections from aged PDAPP mice (25-month old) are incubated with 20 μg/mL of an exemplified N3pGlu Aβ antibody of the present invention (Antibody I or Antibody II). Secondary HRP reagents specific for human IgG are employed and the deposited plaques are visualized with DAB-Plus (DAKO). Biotinylated murine 3D6 antibody followed by Step-HRP secondary is used as a positive control. The positive control antibody (biotinylated 3D6) labeled significant quantities of deposited Aβ in the PDAPP hippocampus, and the exemplified N3pGlu Aβ antibodies of the present invention labeled a subset of deposits. These histological studies demonstrated that the exemplified N3pGlu Aβ antibodies of the present invention engaged deposited Aβ target ex vivo.

Ex Vivo Phagocytosis

An ex vivo phagocytosis assay is performed to investigate whether N3pGlu Aβ antibodies of the present invention (Antibody I or Antibody II) can facilitate microglial phagocytosis of plaque. Frozen sections from human Alzheimer's brain (20 μm) are pre-incubated with 10 μg/mL exemplified N3pGlu Aβ antibody of the present invention or controls for one hour at 37° C. in 24-well plates. There are four wells per treatment. Primary murine microglia cells ($8\times10^5$; C57/BL6) are then added and incubated for 24 hours. Tissue in each well is denatured in 5.2 M guanidine buffer and the $A_{\beta1\text{-}42}$ content is evaluated by ELISA. Since the Aβ content can vary over the span of multiple sections, a sister section control is implemented for every test well and the content of the test well is normalized to that of the sister section.

Compared to the positive control samples, exemplified N3pGlu Aβ antibodies of the present invention had significantly reduced $A\beta_{1\text{-}42}$. The negative control samples had negligible clearance of deposited $A\beta_{1\text{-}42}$. Therefore, ex vivo phagocytosis analyses show that exemplified N3pGlu Aβ antibodies of the present invention can clear plaque ex vivo by phagocytosis.

In Vivo Target Engagement

The ability of N3pG antibodies of the present invention to cross the blood-brain-barrier and bind to deposited plaque in vivo is measured. Eighteen month old PDAPP transgenic mice are given intraperitoneal injections with N3pGlu Aβ antibody (Antibody I or Antibody II) or negative control IgG. Six mice per group receive one 40 mg/kg injection of antibody on day 1 and on day 3. In vivo target engagement is determined on day 6, when mice are sacrificed and brains are collected for histochemical analyses.

The extent of in vivo target engagement is quantified as the percent area positive for the in vivo N3pGlu Aβ antibody engagement normalized to the total plaque area as defined by exogenous 3D6 immunostaining on sister sections (TE Ratio). The TE Ratio is generated by measuring the percent of area bound by the antibody and normalizing the value against the total percent of area of possible target (total deposited Aβ visualized by exogenous immunohistochemistry with a positive control antibody (3D6) on a sister section).

Following procedures essentially as described above, exemplified N3pGlu Aβ antibodies of the present invention demonstrated in vivo target engagement within the hippocampus and to a limited extent in the cortex, whereas the animals injected with control IgG show no plaque-specific staining. The TE Ratios were 1.95% (Antibody I) and 3.65% (Antibody II).

A similar study is performed with Antibody II in PDAPP mice at an average of 24 to 26 months of age. The Antibody II had a TE Ratio of 9.41%.

These results demonstrated that Antibody I and Antibody II, when administered peripherally, can cross the blood-brain barrier and engage deposited Aβ.

In Vivo Plaque Clearance

Studies are performed with chimera surrogate antibodies with LCVR and HCVR of Antibody II fused to murine constant kappa region and IgG2a Fc to evaluate in vivo plaque clearance in aged PDAPP mice. Aged PDAPP mice (22 to 24-months of age, n=23 per group) are injected subcutaneously once a week for 7 weeks with 12.5 mg/kg of chimera Antibody II or control IgG. Control aged PDAPP mice (sacrificed at the onset of the study) are used to evaluate the levels of pre-existing deposition prior to therapeutic treatment.

At the conclusion of the study, final drug levels are measured in plasma, and brains are evaluated by ELISA for levels of $A\beta_{1\text{-}42}$. The aged PDAPP mice are at the plaque ceiling as evidenced by a non-significant further accrual of $A\beta_{1\text{-}42}$ over the 7-week treatment period with the control IgG. Antibody II chimera antibody group shows significant reduction in $A\beta_{1\text{-}42}$ (23%, p=0.0174) compared to control. Antibody exposure level was measured at the end of 7-week dosing period, and Antibody II had a level of 31 μg/mL. This study demonstrated that the exemplified chimera N3pGlu Aβ antibodies are able to lower plaque ($A\beta_{1\text{-}42}$) in vivo.

Ex Vivo T-Cell Proliferation EpiScreen Assay

An EpiScreen™ ex vivo human T-cell assay is used to measure activation (proliferation, cytokine secretion) of human CD4+ T cells in response to exemplified N3pGlu Aβ antibodies of the present invention (Antibody I and Antibody II). EpiScreen™ utilizes samples from 50 healthy donors that best represent the number and frequency of HLA-DR and DQ allotypes expressed in the European/North American and world populations. Two positive controls are included in the assay: humanized A33, a clinical benchmark antibody that shows high levels of immunogenicity in the clinic (73%) and routinely induces 20-30% T-cell response in the EpiScreen assay, and KLH (keyhole limpet hemocyanin), a mitogen-like protein containing neoantigens. A matched buffer negative control is also included in the assay.

The percent of T-cell proliferation is calculated from the average of all positive donor responses observed during the time course (days 5-8). The percent T-cell proliferation was 20% and 98% for the positive controls A33 and KLH, respectively. The percent T-cell proliferation was 14%, 6%, and 8% for B12L, Antibody I, and Antibody II, respectively. These data demonstrate that exemplified N3pGlu Aβ antibodies of the present invention have a reduced T-cell response rate compared to positive controls and B12L.

Non-Specific Binding

N3pGlu Aβ antibodies of the present invention are studied for non-specific binding to live CHO cells by fluorescenceactivated cell sorting (FACS) analysis and non-specific binding to human serum albumin, fibronectin, and human LDL by assays that use Meso Scale Discovery (MSD) technology that provide highly sensitive, precise, and accurate results across a wide dynamic range.

To detect non-specific binding to live CHO cells, FACS analysis is performed. N3pGlu Aβ antibodies (Antibody I, Antibody II, or B12L), are diluted to 200 μg/mL in FACS buffer+0.1% BSA. RPE labeled F(ab')2 donkey anti-human IgG (H+L) secondary antibody is diluted to 20 μg/mL in FACS buffer+0.1% BSA. CHO cells are spun down at 1,000 rpm for 5 minutes, and then washed with FACS buffer+0.1% BSA. Cells are resuspended to $4\times10^6$ cells/mL in FACS buffer+0.1% BSA and 55 μL cell suspension is added into wells of a 96-well plate. Secondary antibody is mixed with N3pGlu Aβ antibody in equal volume and incubated for 1 hour at room temperature. Antibody mixture (55 μL) is added to the cell suspension and incubated for 1 hour at room temperature. Each sample is run in duplicate. Plates are spun, supernatant is discarded, and cells are resuspended in 75 μL FACS buffer+0.1% BSA. Plates are again spun and cells are resuspended in 110 μL FACS buffer+0.1% BSA. Viability dye (Sytox Blue; 1.1 μL is added to each well and mixed prior to FACS analysis. Cell binding activity is measured by FACS analysis using a LSRFortessa™ FACS machine (BD Biosciences).

To detect non-specific binding to human serum albumin, fibronectin, and human LDL, an MSD assay is utilized. Plates (MSD Multiarray 96 well plate: MSD Cat. #L15XA-3) are coated with 30 μL/well of coating protein (20 μg/mL in PBS) overnight at 4° C. Coating proteins can be LDL solution (Lipoprotein, Low Density from Human Plasma, Sigma Cat. #L7914), Fibronectin from bovine plasma (Sigma Cat. #F1141), or HSA (5 mg/mL, Sigma Cat. #A8763). Plates are washed 3 times with PBS+0.1% Tween-20, blocked for 1 hour in PBS+0.5% BSA, and then washed. Antibody I or Antibody II (50 μg/mL; diluted in PBS+0.5% BSA) is added to the wells. Each well is run in duplicate. Plates are incubated at room temperature for 1 hour and then washed. MSD SULFO-TAG anti-human antibody (MSD; catalog number R32AJ-5) is diluted to 1 μg/ml with PBS+0.5% BSA and 50 μL is added to each well. Plates are incubated at room temperature for 1 hour and then washed. MSD read buffer (MSD; catalog number R92TC-3) is diluted in water 1:4 to obtain a 1× working solution, and 150 μL is added to each well. Plates are read, and the average signal is calculated.

Following procedures essentially as described above, the following data were obtained.

TABLE 4

Non-specific binding profile

| Antibody | CHO (MFI) | Albumin (ECIL) | Fibronectin (ECIL) | LDL (ECIL) | Total Score |
|---|---|---|---|---|---|
| I | 107 | 1,686 | 1,512 | 2,972 | 6,277 |
| II | 110 | 1,722 | 2,757 | 2,805 | 7,394 |
| B12L | 287 | 10,140 | 76,055 | 18,617 | 105,099 |

MFI = mean fluorescence intensity;
ECIL = electrochemiluminescence light

The data in Table 4 demonstrate that Antibody I and Antibody II have reduced non-specific binding to live CHO cells, human serum albumin, fibronectin, and human LDL as compared to B12L.

Sequences

Antibody I and Antibody II HCDR1 (SEQ ID NO: 1)
KASGYTFTDYYIN

Antibody I and Antibody II HCDR2 (SEQ ID NO: 2)
WINPGSGNTKYNEKFKG

Antibody I and Antibody II HCDR3 (SEQ ID NO: 3)
TREGETVY

Antibody I and Antibody II LCDR1 (SEQ ID NO: 4)
KSSQSLLYSRGKTYLN

Antibody II LCDR2 (SEQ ID NO: 5)
YAVSKLDS

Antibody I LCDR2 (SEQ ID NO: 6)
YDVSKLDS

Antibody I and Antibody II LCDR3 (SEQ ID NO: 7)
VQGTHYPFT

Antibody I and Antibody II HCVR (SEQ ID NO: 8)
QVQLVQSGAEVKKPGSSVKVSCKASGYTFTDYYINWVRQAPGQGLEWMGWINP
GSGNTKYNEKFKGRVTITADESTSTAYMELS SLRSEDTAVYYCTREGETVYWGQ
GTLVTVSS Antibody I LCVR (SEQ ID NO: 9)
DVVMTQSPLSLPVTLGQPASISCKSSQSLLYSRGKTYLNWFQQRPGQSPRRLIYD
VSKLDSGVPDRFSGSGSGTDFTLKISRVEAEDVGVYYCVQGTHYPFTFGQGTKLE
IK Antibody II LCVR (SEQ ID NO: 10)
DIQMTQSPSTLSASVGDRVTITCKSSQSLLYSRGKTYLNWLQQKPGKAPKLLIYA
VSKLDSGVPSRFSGSGSGTEFTLTISSLQPDDFATYYCVQGTHYPFTFGQGTKLEI
K -continued

| Sequences |
|---|

Antibody I and Antibody II Heavy Chain (SEQ ID NO: 11)
QVQLVQSGAEVKKPGSSVKVSCKASGYTFTDYYINWVRQAPGQGLEWMGWINP
GSGNTKYNEKFKGRVTITADESTSTAYMELSSLRSEDTAVYYCTREGETVYWGQ
GTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHY
TQKSLSLSPG Antibody I Light Chain (SEQ ID NO: 12)
DVVMTQSPLSLPVTLGQPASISCKSSQSLLYSRGKTYLNWFQQRPGQSPRRLIYD
VSKLDSGVPDRFSGSGSGTDFTLKISRVEAEDVGVYYCVQGTHYPFTFGQGTKLE
IKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC Antibody II Light Chain (SEQ ID NO: 13)
DIQMTQSPSTLSASVGDRVTITCKSSQSLLYSRGKTYLNWLQQKPGKAPKLLIYA
VSKLDSGVPSRFSGSGSGTEFTLTISSLQPDDFATYYCVQGTHYPFTFGQGTKLEI
KRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC Exemplified DNA for Expressing Antibody Heavy Chain of SEQ ID NO: 11
(SEQ ID NO: 14)
CAGGTGCAGCTGGTGCAGTCTGGGGCTGAGGTGAAGAAGCCTGGGTCCTCGG
TGAAGGTCTCCTGCAAGGCTTCTGGATACACCTTCACCGACTATTATATCAAC
TGGGTGCGACAGGCCCCTGGACAAGGGCTTGAGTGGATGGGATGGATCAACC
CTGGCAGTGGTAATACAAAGTACAATGAGAAGTTCAAGGGCAGAGTCACGAT
TACCGCGGACGAATCCACGAGCACAGCCTACATGGAGCTGAGCAGCCTGAGA
TCTGAGGACACGGCCGTGTATTACTGTACAAGAGAAGGCGAGACGGTCTACT
GGGGCCAGGGAACCCTGGTCACCGTCTCCTCAGCCTCCACCAAGGGCCCATC
GGTCTTCCCGCTAGCACCCTCCTCCAAGAGCACCTCTGGGGGCACAGCGGCCC
TGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGC
ACCCAGACCTACATCTGCAACGTGAATCACAAGCCCAGCAACACCAAGGTGG
ACAAGAAAGTTGAGCCCAAATCTTGTGACAAAACTCACACATGCCCACCGTG
CCCAGCACCTGAACTCCTGGGGGGACCGTCAGTCTTCCTCTTCCCCCCAAAAC
CCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGC
GTGGAGGTGCATAATGCCAAGACAAAGCCGCGGGAGGAGCAGTACAACAGC
ACGTACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCGAG
AAAACCATCTCCAAAGCCAAAGGGCAGCCCCGAGAACCACAGGTGTACACCC
TGCCCCCATCCCGGGACGAGCTGACCAAGAACCAGGTCAGCCTGACCTGCCT
GGTCAAAGGCTTCTATCCCAGCGACATCGCCGTGGAGTGGGAGAGCAATGGG
CAGCCGGAGAACAACTACAAGACCACGCCCCCCGTGCTGGACTCCGACGGCT
CCTTCTTCCTCTATAGCAAGCTCACCGTGGACAAGAGCAGGTGGCAGCAGGG
GAACGTCTTCTCATGCTCCGTGATGCATGAGGCTCTGCACAACCACTACACGC
AGAAGAGCCTCTCCCTGTCTCCGGGT Exemplified DNA for Expressing Antibody Light Chain of SEQ ID NO: 12
(SEQ ID NO: 15)
GATGTTGTGATGACTCAGTCTCCACTCTCCCTGCCCGTCACCCTTGGACAGCC
GGCCTCCATCTCCTGCAAGTCTAGTCAAAGCCTCCTGTACAGTCGCGGAAAAA
CCTACTTGAATTGGTTTCAGCAGAGGCCAGGCCAATCTCCAAGGCGCCTAATT
TATGATGTTTCTAAACTGGACTCTGGGGTCCCAGACAGATTCAGCGGCAGTGG
GTCAGGCACTGATTTCACACTGAAAATCAGCAGGGTGGAGGCTGAGGATGTT
GGGGTTTATTACTGCGTGCAAGGTACACACTACCCTTTCACTTTTGGCCAAGG
GACCAAGCTGGAGATCAAACGGACCGTGGCTGCACCATCTGTCTTCATCTTCC
CGCCATCTGATGAGCAGTTGAAATCTGGAACTGCCTCTGTTGTGTGCCTGCTG
AATAACTTCTATCCCAGAGAGGCCAAAGTACAGTGGAAGGTGGATAACGCCC
TCCAATCGGGTAACTCCCAGGAGAGTGTCACAGAGCAGGACAGCAAGGACA
GCACCTACAGCCTCAGCAGCACCCTGACGCTGAGCAAAGCAGACTACGAGAA
ACACAAAGTCTACGCCTGCGAAGTCACCCATCAGGGCCTGAGCTCGCCCGTC
ACAAAGAGCTTCAACAGGGGAGAGTGC Exemplified DNA for Expressing Antibody Light Chain of SEQ ID NO: 13
(SEQ ID NO: 16)
GACATCCAGATGACCCAGTCTCCTTCCACCCTGTCTGCATCTGTAGGAGACAG
AGTCACCATCACTTGCAAGTCCAGTCAGAGTCTCCTGTACAGTCGCGGAAAA
ACCTATTTGAACTGGCTCCAGCAGAAACCAGGGAAAGCCCCTAAGCTCCTGA
TCTATGCTGTCTCCAAACTGGACAGTGGGGTCCCATCAAGGTTCAGCGGCAGT
GGATCTGGGACAGAATTCACTCTCACCATCAGCAGCCTGCAGCCTGATGATTT
TGCAACTTATTACTGCGTGCAGGGTACACATTATCCTTTCACTTTTGGCCAGG -continued

| Sequences |
|---|
| GGACCAAGCTGGAGATCAAACGGACCGTGGCTGCACCATCTGTCTTCATCTTC<br>CCGCCATCTGATGAGCAGTTGAAATCTGGAACTGCCTCTGTTGTGTGCCTGCT<br>GAATAACTTCTATCCCAGAGAGGCCAAAGTACAGTGGAAGGTGGATAACGCC<br>CTCCAATCGGGTAACTCCCAGGAGAGTGTCACAGAGCAGGACAGCAAGGACA<br>GCACCTACAGCCTCAGCAGCACCCTGACGCTGAGCAAAGCAGACTACGAGAA<br>ACACAAAGTCTACGCCTGCGAAGTCACCCATCAGGGCCTGAGCTCGCCCGTC<br>ACAAAGAGCTTCAACAGGGGAGAGTGC |
| N3pGlu Aβ (SEQ ID NO: 17)<br>[pE]FRHDSGYEVHHQKLVFFAEDVGSNKGAIIGLMVGGVVIA |

We claim:

1. An antibody that binds human N3pGlu Aβ, comprising a light chain variable region (LCVR) having the amino acid sequence of SEQ ID NO:9 or SEQ ID NO:10, and a heavy chain variable region (HCVR) having the amino acid sequence of SEQ ID NO:8.

2. The antibody of claim 1, comprising a LCVR having the amino acid sequence of SEQ ID NO:9, and a HCVR having the amino acid sequence of SEQ ID NO:8.

3. The antibody of claim 1, comprising a LCVR having the amino acid sequence of SEQ ID NO:10, and a HCVR having the amino acid sequence of SEQ ID NO:8.

4. The antibody of claim 1, comprising a light chain (LC) having the amino acid sequence of SEQ ID NO:12 or SEQ ID NO:13 and a heavy chain (HC) having the amino acid sequence of SEQ ID NO:11.

5. The antibody of claim 1, comprising a LC having the amino acid sequence of SEQ ID NO:12 and a HC having the amino acid sequence of SEQ ID NO:11.

6. The antibody of claim 1, comprising a LC having the amino acid sequence of SEQ ID NO: 13 and a HC having the amino acid sequence of SEQ ID NO:11.

7. The antibody of claim 1, comprising two LCs and two HCs, wherein the amino acid sequence of each LC is SEQ ID NO:12 or SEQ ID NO:13, and the amino acid sequence of each HC is SEQ ID NO:11.

8. The antibody of claim 1, comprising two LCs and two HCs, wherein the amino acid sequence of each LC is SEQ ID NO:12, and the amino acid sequence of each HC is SEQ ID NO:11.

9. The antibody of claim 1, comprising two LCs and two HCs, wherein the amino acid sequence of each LC is SEQ ID NO: 13, and the amino acid sequence of each HC is SEQ ID NO:11.

10. A pharmaceutical composition comprising the antibody of claim 1 and one or more pharmaceutically acceptable carriers, diluents or excipients.

11. A method of treating a patient having a disease characterized by deposition of Aβ, comprising administering to said patient an effective amount of the antibody of claim 1.

12. A method of treating a patient having a condition selected from clinical or pre-clinical Alzheimer's disease, Down's syndrome, and clinical or pre-clinical cerebral amyloid angiopathy, comprising administering to said patient an effective amount of the antibody of claim 1.

13. A method of treating a patient having a condition selected from prodromal AD, mild AD, moderate AD, and severe AD, comprising administering an effective amount of the antibody of claim 1.

14. A method of treating a patient having a condition selected from clinical or pre-clinical Alzheimer's disease, Down's syndrome, and clinical or pre-clinical cerebral amyloid angiopathy, comprising administering to said patient an effective amount of a pharmaceutical composition of claim 10.

15. A method of treating a patient having a condition selected from prodromal AD, mild AD, moderate AD, and severe AD, comprising administering to said patient an effective amount of a pharmaceutical composition of claim 10.

16. A method of slowing cognitive decline in a patient diagnosed with a condition selected from clinical or pre-clinical Alzheimer's disease, Down's syndrome, and clinical or pre-clinical cerebral amyloid angiopathy, comprising administering to said patient an effective amount of the antibody of claim 1.

17. A method of slowing cognitive decline in a patient diagnosed with a condition selected from prodromal AD, mild AD, moderate AD and severe AD, comprising administering to said patient an effective amount of the antibody of claim 1.

18. A method of slowing cognitive decline in a patient diagnosed with a condition selected from clinical or pre-clinical Alzheimer's disease, Down's syndrome, and clinical or pre-clinical cerebral amyloid angiopathy, comprising administering to said patient an effective amount of a pharmaceutical composition of claim 10.

19. A method of slowing cognitive decline in a patient diagnosed with a condition selected from prodromal AD, mild AD, moderate AD and severe AD, comprising administering to said patient an effective amount of a pharmaceutical composition of claim 10.

* * * * *

SEQUENCE LISTING

```
<160> NUMBER OF SEQ ID NOS: 17

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Lys Ala Ser Gly Tyr Thr Phe Thr Asp Tyr Tyr Ile Asn
1               5                   10


<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Asn Pro Gly Ser Gly Asn Thr Lys Tyr Asn Glu Lys Phe Lys
1               5                   10                  15

Gly


<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Thr Arg Glu Gly Glu Thr Val Tyr
1               5


<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Lys Ser Ser Gln Ser Leu Leu Tyr Ser Arg Gly Lys Thr Tyr Leu Asn
1               5                   10                  15


<210> SEQ ID NO 5
<211> LENGTH: 8
<212> TYPE: PRT
<213> ORGANISM: Artificial Sequence
```

<220> FEATURE:
<223> OTHER INFORMATION: Synthetic Construct

<400> SEQUENCE: 5

```
Tyr Ala Val Ser Lys Leu Asp Ser
1               5
```

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

```
Tyr Asp Val Ser Lys Leu Asp Ser
1               5
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

```
Val Gln Gly Thr His Tyr Pro Phe Thr
1               5
```

<210> SEQ ID NO 8
<211> LENGTH: 115
<212> TYPE: PRT
<213> ORGANISM: Artificial Sequence
<220> FEATURE:
<223> OTHER INFORMATION: Synthetic Construct

<400> SEQUENCE: 8

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Glu Thr Val Tyr Trp Gly Gln Gly Thr Leu Val Thr
            100                 105                 110

Val Ser Ser
        115
```

<210> SEQ ID NO 9
<211> LENGTH: 112
<212> TYPE: PRT
<213> ORGANISM: Artificial Sequence
<220> FEATURE:
<223> OTHER INFORMATION: Synthetic Construct

<400> SEQUENCE: 9

```
Asp Val Val Met Thr Gln Ser Pro Leu Ser Leu Pro Val Thr Leu Gly
```

```
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Phe Gln Gln Arg Pro Gly Gln Ser
        35                  40                  45

Pro Arg Arg Leu Ile Tyr Asp Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110


<210> SEQ ID NO 10
<211> LENGTH: 112
<212> TYPE: PRT
<213> ORGANISM: Artificial Sequence
<220> FEATURE:
<223> OTHER INFORMATION: Synthetic Construct

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
            20                  25                  30

Arg Gly Lys Thr Tyr Leu Asn Trp Leu Gln Gln Lys Pro Gly Lys Ala
        35                  40                  45

Pro Lys Leu Leu Ile Tyr Ala Val Ser Lys Leu Asp Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Val Gln Gly
                85                  90                  95

Thr His Tyr Pro Phe Thr Phe Gly Gln Gly Thr Lys Leu Glu Ile Lys
            100                 105                 110


<210> SEQ ID NO 11
<211> LENGTH: 444
<212> TYPE: PRT
<213> ORGANISM: Artificial Sequence
<220> FEATURE:
<223> OTHER INFORMATION: Synthetic Construct

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Thr Arg Glu Gly Glu Thr Val Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

<210> SEQ ID NO 12
<211> LENGTH: 219
<212> TYPE: PRT
<213> ORGANISM: Artificial Sequence
<220> FEATURE:
<223> OTHER INFORMATION: Artifical Sequence

<400> SEQUENCE: 12

```
Asp Val Val Met Thr Gln Ser Pro Leu Ser Leu Pro Val Thr Leu Gly
1               5                   10                  15
```

```
Gln Pro Ala Ser Ile Ser Cys Lys Ser Ser Gln Ser Leu Leu Tyr Ser
            20                  25                  30

Arg Gly Lys Thr Tyr Leu Asn Trp Phe Gln Gln Arg Pro Gly Gln Ser
        35                  40                  45

Pro Arg Arg Leu Ile Tyr Asp Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 13
<211> LENGTH: 219
<212> TYPE: PRT
<213> ORGANISM: Artificial Sequence
<220> FEATURE:
<223> OTHER INFORMATION: Artifical Sequence

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
            20                  25                  30

Arg Gly Lys Thr Tyr Leu Asn Trp Leu Gln Gln Lys Pro Gly Lys Ala
        35                  40                  45

Pro Lys Leu Leu Ile Tyr Ala Val Ser Lys Leu Asp Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 14
<211> LENGTH: 1332
<212> TYPE: DNA
<213> ORGANISM: Artificial Sequence
<220> FEATURE:
<223> OTHER INFORMATION: Synthetic Construct

<400> SEQUENCE: 14

```
caggtgcagc tggtgcagtc tggggctgag gtgaagaagc ctgggtcctc ggtgaaggtc     60

tcctgcaagg cttctggata caccttcacc gactattata tcaactgggt gcgacaggcc    120

cctggacaag ggcttgagtg gatgggatgg atcaaccctg gcagtggtaa tacaaagtac    180

aatgagaagt tcaagggcag agtcacgatt accgcggacg aatccacgag cacagcctac    240

atggagctga gcagcctgag atctgaggac acggccgtgt attactgtac aagagaaggc    300

gagacggtct actggggcca gggaaccctg gtcaccgtct cctcagcctc caccaagggc    360

ccatcggtct tcccgctagc accctcctcc aagagcacct ctgggggcac agcggccctg    420

ggctgcctgg tcaaggacta cttccccgaa ccggtgacgg tgtcgtggaa ctcaggcgcc    480

ctgaccagcg gcgtgcacac cttcccggct gtcctacagt cctcaggact ctactccctc    540

agcagcgtgg tgaccgtgcc ctccagcagc ttgggcaccc agacctacat ctgcaacgtg    600

aatcacaagc ccagcaacac caaggtggac aagaaagttg agcccaaatc ttgtgacaaa    660

actcacacat gcccaccgtg cccagcacct gaactcctgg ggggaccgtc agtcttcctc    720

ttccccccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acaacagcac gtaccgtgtg    900

gtcagcgtcc tcaccgtcct gcaccaggac tggctgaatg gcaaggagta caagtgcaag    960

gtctccaaca aagccctccc agcccccatc gagaaaacca tctccaaagc caaagggcag   1020

ccccgagaac cacaggtgta caccctgccc ccatcccggg acgagctgac caagaaccag   1080

gtcagcctga cctgcctggt caaaggcttc tatcccagcg acatcgccgt ggagtgggag   1140

agcaatgggc agccggagaa caactacaag accacgcccc ccgtgctgga ctccgacggc   1200

tccttcttcc tctatagcaa gctcaccgtg gacaagagca ggtggcagca ggggaacgtc   1260

ttctcatgct ccgtgatgca tgaggctctg cacaaccact acacgcagaa gagcctctcc   1320

ctgtctccgg gt                                                       1332
```

<210> SEQ ID NO 15
<211> LENGTH: 657
<212> TYPE: DNA
<213> ORGANISM: Artificial Sequence
<220> FEATURE:
<223> OTHER INFORMATION: Synthetic Construct

<400> SEQUENCE: 15

```
gatgttgtga tgactcagtc tccactctcc ctgcccgtca cccttggaca gccggcctcc     60
```

atctcctgca agtctagtca aagcctcctg tacagtcgcg gaaaaaccta cttgaattgg 120
tttcagcaga ggccaggcca atctccaagg cgcctaattt atgatgtttc taaactggac 180
tctggggtcc cagacagatt cagcggcagt gggtcaggca ctgatttcac actgaaaatc 240
agcagggtgg aggctgagga tgttggggtt tattactgcg tgcaaggtac acactaccct 300
ttcacttttg gccaagggac caagctggag atcaaacgga ccgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgc 657

<210> SEQ ID NO 16
<211> LENGTH: 657
<212> TYPE: DNA
<213> ORGANISM: Artificial Sequence
<220> FEATURE:
<223> OTHER INFORMATION: Synthetic Construct

<400> SEQUENCE: 16
gacatccaga tgacccagtc tccttccacc ctgtctgcat ctgtaggaga cagagtcacc 60
atcacttgca agtccagtca gagtctcctg tacagtcgcg gaaaaaccta tttgaactgg 120
ctccagcaga aaccagggaa agcccctaag ctcctgatct atgctgtctc caaactggac 180
agtggggtcc catcaaggtt cagcggcagt ggatctggga cagaattcac tctcaccatc 240
agcagcctgc agcctgatga ttttgcaact tattactgcg tgcagggtac acattatcct 300
ttcacttttg gccaggggac caagctggag atcaaacgga ccgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgc 657

<210> SEQ ID NO 17
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 = pyroglutamic acid

<400> SEQUENCE: 17

Xaa Phe Arg His Asp Ser Gly Tyr Glu Val His His Gln Lys Leu Val
1 5 10 15

Phe Phe Ala Glu Asp Val Gly Ser Asn Lys Gly Ala Ile Ile Gly Leu
20 25 30

Met Val Gly Gly Val Val Ile Ala
35 40